United States Patent [19]

Jacoby

[11] Patent Number: 4,940,046
[45] Date of Patent: Jul. 10, 1990

[54] POST-OPERATIVE BUNION SPLINT

[76] Inventor: Richard P. Jacoby, 6021 E. Mockingbird La., Paradise Valley, Ariz. 85253

[21] Appl. No.: 551,331

[22] Filed: Nov. 14, 1983

Related U.S. Application Data

[62] Division of Ser. No. 226,364, Jan. 19, 1981, Pat. No. 4,414,964.

[51] Int. Cl.$^5$ .................. A61F 5/00; A61F 5/30; A61B 19/00
[52] U.S. Cl. .................. 128/81 R; 128/882; 128/891
[58] Field of Search .................. 128/81 R, 149, 153, 128/133

[56] References Cited

U.S. PATENT DOCUMENTS

| | | | |
|---|---|---|---|
| 826,515 | 7/1906 | Litch | 128/81 R |
| 892,412 | 7/1908 | Farra | 128/81 R |
| 1,373,211 | 3/1921 | Tanner | 128/81 R |
| 1,785,185 | 12/1930 | Day | 128/81 R |
| 2,190,016 | 2/1940 | Day et al. | 128/81 R |
| 2,232,473 | 10/1943 | Salander | 128/81 R |
| 2,464,457 | 3/1949 | Madaio | 128/153 |
| 2,888,013 | 5/1959 | Levitt | 128/153 |
| 3,049,120 | 8/1962 | Marcus | 128/81 R |
| 3,063,446 | 11/1962 | Levitt | 128/81 R |
| 3,110,306 | 11/1963 | Posner | 128/153 |
| 4,414,964 | 11/1983 | Farino et al. | 128/81 R |

Primary Examiner—Stephen C. Pellegrino
Assistant Examiner—C. W. Shedd
Attorney, Agent, or Firm—Richard R. Mybeck

[57] ABSTRACT

A post-operative pliable protector device for the hallux or big toe of a patient has a cushion pad with at least a portion thereof adapted to encircle the toe and formed with separable fastener (of the type marketed by Velcro, USA, Manchester, N.H.) having its loop-type fabric component fastened to and covering the backside of the pad and a strip of its hook-type fabric component fastened onto the front side of the pad across one end of the pad portion. A stiffening stay strip member may be fastened transversely across the backside of the pad portion at a location thereon generally medially between its opposite ends. The cushion pad may also have a rearwardly extending portion for encircling and fastening around the forefoot as by a similar hook/loop type separable fastener. A separate strip or tape of the hooked-type fastener fabric material may be fastened taut across the toe and forefoot encircled portions of the applied protector device to shift the toe from its normal position and hold it in a desired displaced position.

10 Claims, 3 Drawing Sheets

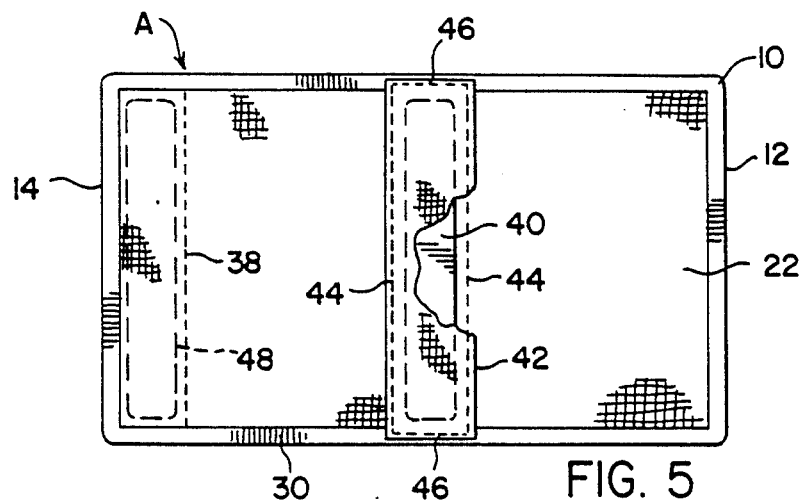
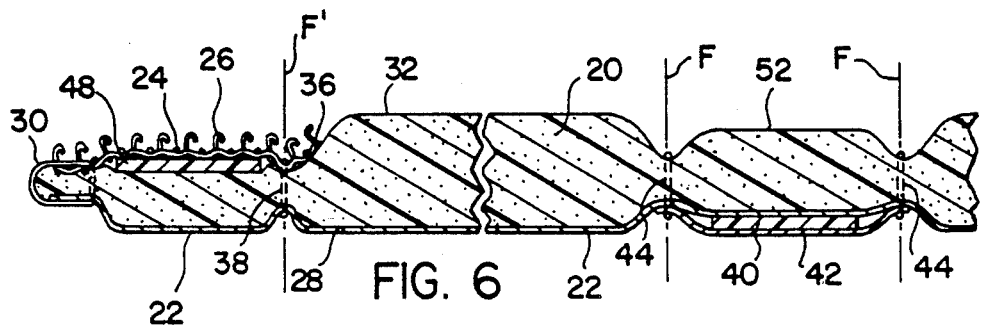
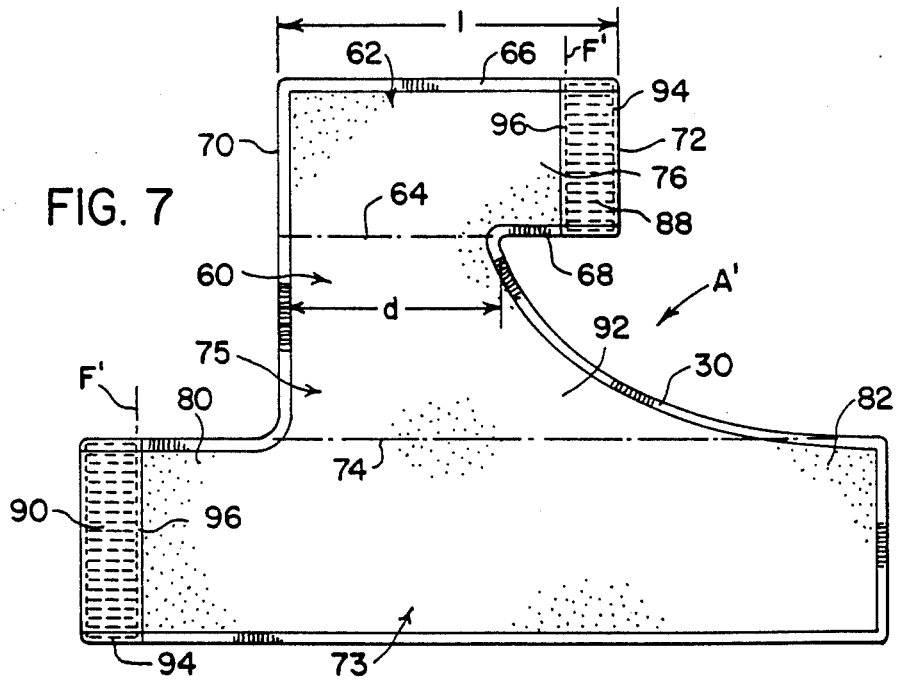

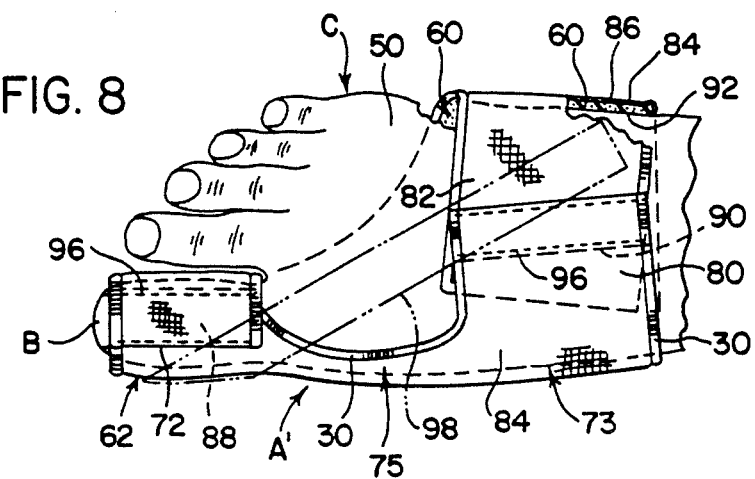
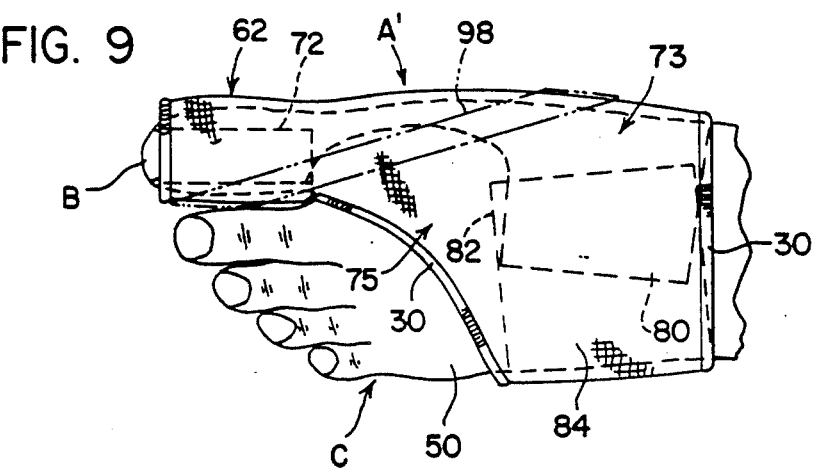

POST-OPERATIVE BUNION SPLINT

This application is a division out of Ser. No. 226,365 filed Jan. 19, 1981 now U.S. Pat. No. 4,414,964.

BACKGROUND OF THE INVENTION

This invention relates in general to a surgical splint or bandage device for protecting a pedal digit such as the hallux or big toe of a patent following surgical or other operations performed thereon.

In many instances following surgical treatment of a pedal digit such as the hallux or big toe of a human being, for example, the correction of hallux abducto valgus or so-called bunions, it is customary and sometimes necessary to apply a protective splint device or bandage of some sort over the toe in order to prevent injury thereto and mitigate against pain caused by pressure against the surgically treated toe such as exerted, for example, by adjacent toes or by a shoe worn on the patent's foot. Heretofore, such toe protector devices generally have been formed by hand from a small pad of plastic foam or other cushion material folded around the toe and held in place thereon as by wrapping a strip of surgical gauze or other fabric material around the cushioned pad encircling the toe. However, because of the close proximity of a patient's big toe to the adjacent toe and the difficulty of maintaining them spread apart to permit the insertion therebetween and wrapping of the protector device and the gauze or other fabric retaining material around the big toe, the application of such hand-formed protector devices to a patient's big toe has been a rather cumbersome and time consuming operation, especially in self-application instances. Such application difficulty, moreover, is compounded each time such a hand-applied toe protector device has to be removed and replaced, for example, when the patient wishes to bathe.

Toe straightening devices are known in the art, such as illustrated in U.S. Pat. No. 2,958,324 to Berkemann, which also afforded a limited degree of toe protection when in use. However, such devices, where comprised in part of a rigid molded plastic member as shown in the above-mentioned patent, are not only comparatively expensive and cumbersome as well as uncomfortable in use but also interfere with the wearing of a slipper or shoe or other footwear over the applied device.

SUMMARY OF THE INVENTION

The present invention contemplates a new and improved form of a toe protector or surgical splint device which overcomes all of the above-mentioned problems and others characteristic of prior such devices, and provides a toe protector device which is of simple one-piece form and easily and quickly applicable to a patient's toe and foot even by the patient alone, and which is not unduly uncomfortable in use and readily permits the wearing of a slipper or other footwear thereover.

Briefly stated, in accordance with one aspect of the invention, a pliable toe protector or surgical splint device is provided comprised of a pad of soft cushion material, such as a plastic foam or sponge rubber material, having a hook/loop type separable fastener attached thereto for enabling quick and easy application of the device in place around and securing it to a patient's toe as well as ready detachment therefrom. The separable fasteners manufactured and sold by Velcro, U.S.A., Manchester, N.H. under the brand name VELCRO ®, in which a tape member having a plurality of woven hooks is adapted to engage and coact with the loops of a brushed loop fabric member to form therewith a fastener, is highly suitable for use in the present invention. Such a fastener shall hereinafter be denominated a "hook/loop" fastener.

According to a further aspect of the invention, a narrow stiffening stay strip member may be fastened transversely across the backside of the toe-encircling cushion pad in the medial region thereof between its opposite ends for the purpose of imparting a degree of self-support to the device and sufficient stiffness to keep the protected toe aligned with the patient's forefoot. Advantageously, the protector device may also be provided with a plurality of transverse lines of weakness forming parallel fold lines including a pair extending alongside opposite sides of the stay strip member and another extending alongside the strip of the hook-type fabric material of the Velcro ® fastener. The fold lines permit ready folding and wrapping of the device around the toe and interlocking engagement of the two component sections of the fastener means on the protector device so as to hold it securely in place in its folded position around the patient's toe.

According to a still further feature of the invention, the cushion pad also may be provided with a rearwardly extending portion for encircling and fastening around the forefoot as by a hook/loop type separable fastener. A separate strip of the hook-type fastener material may be employed for attachment to and between the toe-encircled and foot-encircled portions of the cushion pad to shift the toe from its normal position and hold it in a desired shifted position.

The principal object of the invention is to provide a one-piece toe protector device of simple and low cost form which can be quickly and conveniently applied repeatedly to and detached from the large toe of a patient's foot by either the patient himself or by another person.

Another object of the invention is to provide a toe protector device of the type referred to which does not form a bulky and discomforting bandage on a patient's large toe yet affords adequate protection thereof from shoe pressure as well as from pressure of the adjacent toe of the patient.

Still another object of the invention is to provide a toe protector device of the type referred to which, in its applied state folded around a patient's large toe, presents a soft cushion pad surface throughout to, and in contact with the surface of the toe to minimize pain from any external pressure applied to the toe.

A further object of the invention is to provide a toe protector device of the type referred to which can be adjusted to shift and hold the toe in a position other than its normal position.

Further objects and advantages of the invention will appear from the following detailed description of a preferred embodiment thereof and from the accompanying drawings which form a part hereof.

BRIEF DESCRIPTION OF THE DRAWINGS

In the drawings:

FIG. 5 is a rear plan view of the toe protector device of FIG. 3 with a portion thereof shown broken away;

FIG. 6 is a longitudinal sectional view on an enlarged scale taken on the line 6—6 of FIG. 3;

FIG. 7 is a front plan view of a modified form of a toe protector device comprising the invention prior to its application to a patient's toe; and, FIGS. 8 and 9 are top views showing the modified device of FIG. 7 applied to the large toe of a patient's right and left foot, respectively.

DESCRIPTION OF THE PREFERRED EMBODIMENTS

Figure 1:
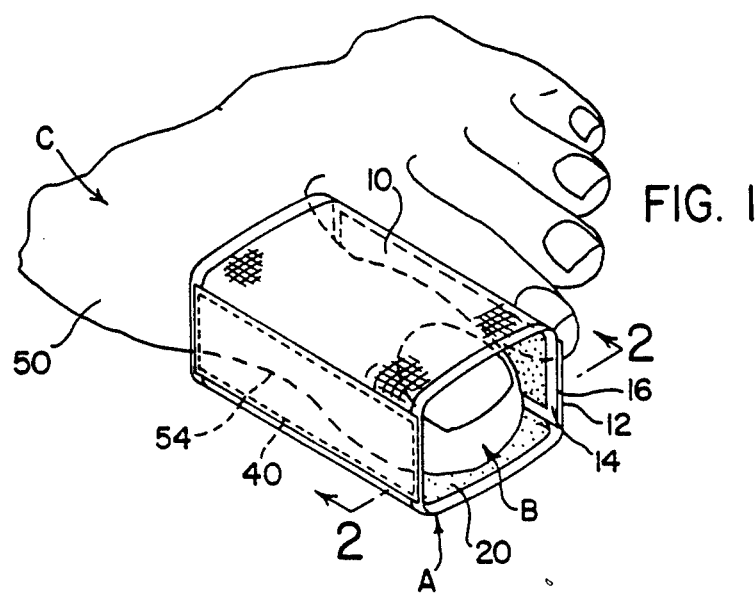
FIG. 1 is a perspective view illustrating a toe protector device comprising the invention applied to a patient's large toe.
Figure 2:
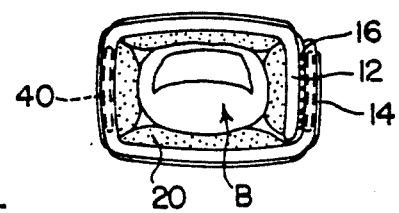
FIG. 2 is a front and elevation of the applied protector device taken on the line 2—2 of FIG. 1.
Figure 3:
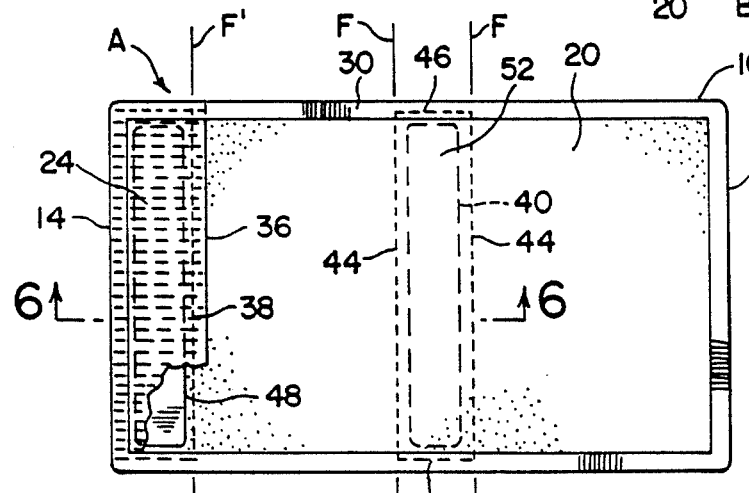
FIG. 3 is a front plan view of the toe protector device comprising the invention prior to its application to a patient's toe, with a portion of the device shown partly broken away.
Figure 4:
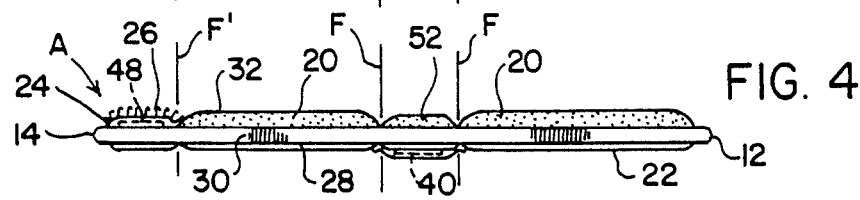
FIG. 4 is a side elevation of the toe protector device shown in FIG. 3.

Referring now to the drawings wherein the showings are for the purpose of illustrating preferred embodiments of the invention only and not for the purpose of limiting same, FIGS. 1 and 2 illustrate a toe protector or surgical splint device A according to the invention applied onto a pedal digit or large toe B of a patient's foot C, for protection purposes such as following surgical operations performed on the toe. The toe protector device A is in the form of a strip-shaped pliable body 10 which, as shown, is folded and snugly wrapped in a single turn around the toe B, with its opposite end portions 12 and 14 slightly overlapped and detachably fastened together along their interface, as indicated at 16. The detachable fastening of the overlapped end portions 12, 14 of the folded-over body 10 is preferably accomplished by providing the interfacing surfaces of the overlapped body end portions 12, 14 with hook/loop separable fastener surface components which interlock and hold tight with one another when firmly pressed together in face-to-face relation but can be readily peeled apart and separated when desired. Such hook/loop separable fasteners with interlockable surfaces are well known and disclosed in U.S. Pat. Nos. 2,717,47; 3,000,384; and, 3,009,235.

Referring now to FIGS. 3-6, the toe protector or surgical splint device A comprises a generally rectangular-shaped pad 20 of a soft synthetic resin cushion material such as, for example, a soft foam plastic material or sponge rubber, to the opposite side surfaces of which are respectively fastened the two component fabric surface elements, i.e., the looped-type and hooked-type fabric sections or layers 22, 24, respectively, of a conventional hook/loop separable fastener device such as disclosed in the aforementioned patents. The looped-type fabric layer 22 of such separable fasteners is one characterized by the presence of a great many minute outwardly projecting loops (not shown) formed by certain ones of the filamentary threads of the fabric that are preferably made of nylon or other thermosetting synthetic resin material capable of being set by heat into a predetermined form. The hooked-type fabric layer 24 is characterized by the presence of a great many outwardly projecting hooks 26 (FIGS. 4 and 6) likewise formed in certain ones of the filamentary threads of the fabric similarly made of nylon or other thermosetting synthetic resin and heated to set the filamentary hooks in a more or less self-supporting but somewhat flexible condition. The primary or base fabric of such a hooked-type fabric layer material 24 may comprise a plastic cloth. When the two layers 22, 24 are pressed together in face-to-face relation, a substantial percentage of the hooks and loops interengage and become locked with one another, thereby firmly adhering the surfaces together. However, they may be readily separated simply by peeling them apart.

The looped-type fastener fabric layer 22 covers and is fastened to the backside or surface 28 of the cushion pad 20 in any suitable manner, for instance, by and edge binding or stitched overcasting 30. Preferably, the looped-type fabric backing layer 22 and the cushion pad 20 may be fabricated of a material such as that commercially known as VELCRO ® foam wherein the fabric layer 22 is bonded to a foam plastic pad 20 by an adhesive to form a composite material. A suitable one such composite material is that designated as VF-53 Velfoam ® I of ¼ inch thickness and manufactured by Smalley and Bates, Inc. of Nutley, N.J.

The hooked-type fastener fabric layer 24 is in the form of a strip overlying and fastened to the front side 32 of the cushion pad 20 across one end 14 thereof, also as by means of the edge binding or stitched overcasting 30. The hooked-type fabric layer 22 by a stitched seam 38.

A narrow stiffening stay strip member 40, such as a somewhat flexible resilient plastic strip, is preferably fastened flatwise on the backside 28 of the cushion pad 20 in a position extending transversely thereacross and generally medially between the opposite ends 12, 14 of the pad. As shown in FIGS. 5 and 6, the stay strip member 40 may be secured in place on the pad 20 by an overlying strip of cloth fabric 42 stitched to the pad and fabric backing layer 22 thereon along stitch lines 44 extending transversely across the pad 20 alongside the stay strip member 40. The fastening cloth strip 42 also may be stitched across its ends to the pad 20 and fabric backing layer 22 along stitch lines 46. A similar stiffening stay strip member 48 may be fastened to the front side 32 of the cushion pad 20 underneath the hook-type fabric end strip 24.

In the applied position of the toe protector device A on a patient's large or big toe B, the stiffening stay member 40 is located in a position extending alongside the outer medial side of the patient's toe to aid in maintaining the toe aligned with the patient's forefoot 50. The transverse stitch lines 44, which secure the fastening fabric strip 42 for the stay strip 40 to the cushion pad 20 and backing fabric layer 22, form lines of weakness in the pad which serve as fold lines F therefor to enable ready folding or wrapping of the toe protector device A in proper oriented position around the toe B of the patient. The stitched seam line 38 fastening the hooked-type fastener fabric strip 24 to the cushion pad 20 also forms a transverse line of weakness in the pad serving as an additional fold line F' therefor to also facilitate the folding or wrapping of the toe protector device A around the patient's toe B and to further facilitate the pressure securing of the fastener sections 22, 24 together. The fold line F' also serves to minimize the inherent straightening forces in the cushion pad 20 tending to unfold and separate the fastener sections 22, 24 from one another and thus unloosen the toe protector device A from around the patient's to B.

In the application of the toe protector device A of FIGS. 3-6 to the large toe B of a patient, they stay-reinforced mid-section 52 of the device A is first positioned and held firmly against the outer medial side 54 of the toe B in a position extending longitudinally alongside the toe side 54. The end 12 of the device A opposite the end 14 carrying the hooked-type fabric layer strip 24 of the fastener is then folded around the toe B, after which the other end 14 of the device A provided with the hooked-type fabric end strip 24 thereon is then folded around the toe B to overlap the end 12 of the device A and pressed firmly thereagainst to interlock and adhere thereto, thus securing the device A in place on the toe. The applied device A thus provides a protective sheath for the patient's toe which is of minimal bulkiness and which can be applied quickly and in a simple and facile manner and which will remain in place tightly wrapped around the patient's toe. Because of the easily separable fastener elements 22, 24, the two ends 12, 4 of the protector device A can be readily separated and the device unloosened and removed from around the patient's toe B when desired, as when the patient wishes to bathe, and subsequently replaced. If desired, a protective underlayer (not shown) of a sterile bandaging material such as cotton gauze fabric may be placed or wrapped around the patient's toe, covering any incision therein, before applying the surgical splint or toe protector device therearound.

The modified form of toe protector device A' shown in FIGS. 7-9 comprises a cushion pad 60 of the same material as the pad 20 in FIGS. 1-6. The pad 60 includes a generally rectangular-shaped toe-engaging area portion 62 (as delineated in part in FIG. 7 by the dash dot line 64) having opposite side edges 66, 68 and ends 70, 72, for wrapping around the hallux or big toe B of a patient. The pad 60 also includes a generally rectangular-shaped forefoot engaging area portion 73 (as delineated in part in FIG. 7 by the dash-dot line 74) extending parallel to the toe-engaging portion 62, for wrapping around the metatarsus or forefoot 50 of a patient. The forefoot-engaging area portion 73 is shown in FIGS. 7-9 as being joined to the toe-engaging area portion 62 by a connecting area portion 75 of the pad 60 extending from one of the side edges 66, 68 (e.g. side edge 68 in FIG. 7), of the rectanglular area portion 62. The connecting area portion 75 is of appreciably less lateral dimension d than the length 1 of the rectangular area portion 62, at the junction therewith at the side edge 68 and along the line 64, so as to form an end portion 76 of the rectangular area portion 62 as a projecting lateral flap portion. The forefoot-engaging pad portion 74 terminates at its opposite ends in laterally extending wing portions 80 and 82 for wrapping around the metatarsus or forefoot of a patient.

Hook/loop separable fastener means are attached to the pad 60 comprised, in part, of a looped-type woven fabric layer 84 (FIG. 8), the same as the fabric layer 22 in FIGS. 1-6, covering and fastened to the backside or surface 86 of the pad 60 by an edge binding or stitched overcast 30. End strip sections 88, 90 of hooked-type woven fabric, the same as the hooked-type woven fabric strip 24 in FIGS. 1-6, are respectively fastened to the front surface 92 (FIG. 8) of the pad 60 across the outward or free flap end 72 of the rectangular toe-engaging area portion 62, and across the outward free end of one or the other of the lateral wings 80, 82 of the forefoot-engaging area portion 73 of the pad 60, preferably across the wing 80 which project from the pad in a direction opposite to that of the projecting flap portion 76, as shown. The hooked type fabric strips 88, 90 are fastened around their edges to the front side of the pad 60 by stitched seams 94. The portions 96 of the seams 94 which extend transversely across the end flap 76 and the lateral wing portion 80, along the inner side edges of the hooked-type fabric strips 8, 90, for transverse lines of weakness in pad 60 serving as fold lines F' therefor to facilitate the folding or wrapping of the toe-engaging portion 62 of the pad around the patient's toe B and to facilitate the pressure securing the fastener strip sections 88, 90 to the backing layer 84 to lock them together.

In the application of the modified toe protector device A' to the large toe B of a patient, the forefoot-engaging and connector portions 73, 75 of the device are placed either on top or beneath the forefoot 50 (depending on whether it is to be applied to the right or left foot), with the rectangular toe-engaging area portion 62 positioned abreast of the toe B. The portion 62 is then wrapped or folded snugly around the toe as shown in FIGS. 8 and 9 with the hooked-type fabric end strip 88 on the flap end 76 of portion 62 overlapping and overlying the other end 70 of the portion 62, as shown in FIGS. 8 and 9. The fabric end strip 88 is then pressed firmly against the looped-type fabric backing layer 84 on the pad 60 to interlock and ahdere thereto, thus securing the toe-engaging area portion 62 of the device A' in place around the toe. Thereupon, the lateral wing portions 80 and 82 of the forefoot-engaging area portion 73 of the pad 60 are folded snugly around the patient's forefoot 50 and overlapped, and the hooked-type fabric end strip 90 on the wing portion 80 then pressed firmly against the looped-type fabric backing layer 84 on the other wing portion 82 to interlock and adhere thereto, thus securing the forefoot area engaging portion 73 in place around the forefoot 50. The forefoot-engaging portion 73 of the protector device A' thus aids in holding the toe-enclosing portion 62 of the device in proper toe-enclosing position on the patient's toe B against undersire endwise dislodgement therefrom.

In cases where it may be desirable, while the toe protector device A' is in place around a patient's toe B, to position and hold the toe in a slightly displaced position, i.e. upward or sideward, from its normal position, a positioning tape or strap member 98 of hooked-type fastener fabric material, as shown in dash-dot lines in FIGS. 8 and 9, may be fastened at one end to the inward or outward side of the toe-enclosing portion 62 of the applied device A' and then pulled taut in the required direction to effect the desired displacement or positioning of the patient's toe B relative to the forefoot 50, and the other end of the tautened tape 98 then secured to the forefoot-enclosing portion 73 of the applied protector device A'. If desired, the toe positioning tape or strap member 98 may be employed as the sole means connecting or tying the toe and forefoot-engaging portions 62, 73 of the device together on the foot of a patient, the intermediate connecting portion 75 of the pad 60 in such case being eliminated and the toe-engaging and forefoot-engaging portions 62, 73 formed instead as separate elements subsequently interconnected by the positioning tie strap 98.

The protective splint device A' as thus described above is an excellent adjunct in post-operative splinting following correction of hallux abducto valgus. Not only does it maintain correction in any axis of motion but the bindings restrict abduction and valgus rotation while allowing for flexion and extension. The adjustable V-strap 98 allows for patient comfort control while aiding in post-operative security of the surgical site. Also, the materials employed for the splint device are biologically compatible and hypo-allergenic, and the contours of the splint are well suited to the anatomical structures to which it is to be applied.

It is understood that such modifications, alterations and adaptations, as may readily occur to the artisan skilled in the field to which this invention pertains when confronted with this specification, are intended within the spirit of the present invention which is limited only by the scope of the claims appended hereto.

What is claimed is:

1. A toe protector device comprising a generally rectangular toe-enclosing pad portion of cushion material having opposite ends for wrapping around the toe of a patient and a generally rectangular-shaped forefoot-engaging pad portion of cushion material for wrapping around the forefoot of the patient, hook-loop separable fastener means on said toe-engaging and forefoot-engaging pad portions for holding them in place wrapped around the toe and forefoot of the patient, and connector means tying said pad portions together in place on the toe and forefoot of the patient; said conecctor means having a separate tie strap of hooked-type fastener fabric material connectable to said toe-engaging and forefoot-engaging pad portions in a selected tautened position therebetween to locate and hold the toe of the patient in a desired position relative to the forefoot of the patient.

2. A toe protector device as specified in claim 1 wherein the said connector means further includes an intermediate cushion pad portion integral with the said toe-engaging and forefoot-engaging pad portions of the device.

3. A toe protector device as specified in claim 2 wherein the said intermediate pad portion is of appreciably less lateral dimension than the longitudinal extent of said toe-engaging pad portion at the junction therewith so as to constitute a portion of the length of said toe-engaging pad portion as a projecting flap portion.

4. A toe protector device as specified in claim 3 wherein one of said hook/type fastener means comprises a strip of hooked-type woven fabric material fastened across the free outward end of the said projecting flap portion of said toe-engaging pad portion.

5. A device according to claim 1 in which said hook/loop separable fastener means is made of Velcro ® material.

6. A toe protector device comprising a pad of cushion material having front and back surfaces and including a generally rectangular-shaped toe-enclosing area portion having opposite ends for wrapping around the toe of a patient and a forefoot-engaging area portion extending from one of the longer sides of said rectangular area portion and being of appreciably less lateral dimension than the longitudinal extent of said rectangular area portion at the junction therewith so as to constitute a portion of the length of said rectangular area portion as a projecting flap portion, said forefoot-engaging pad portion terminating in laterally extending wing portions which are generally parallel to said longer sides and are for wrapping around the forefoot of a patient, said wing portions each having an outward end which is generally parallel to the shorter sides of said rectangular area portion, hook/loop separable fastener means attached to said pad and comprising a looped-type woven fabric backing section covering and fastened to the back surface of said pad and having filamentary loops of flexible filamentary material, and end strip sections of hooked-type woven fabric material respectively fastened to the front surface of said pad across one end of said rectangular toe-engaging area portion thereof and across the outward end of one of said wing portions thereof, said hooked-type woven fabric end strip sections having a multiplicity of small outwardly projecting filamentary hooks of flexible resilient material for interlocking engagement with the loops of said looped-type fabric backing section when the opposite ends of said toe-enclosing portion and said forefoot engaging wing portions are respectively overlapped and their hooked-type end strip sections engaged with and pressed against the looped-type backing section of said pad.

7. A toe protector device as specified in claim 6 and comprising, in addition, a separate strip of said hooked-type woven fabric material for stretching taut across and interlockingly engaging at its opposite ends with the looped-type fabric backing section of said toe-engaged and forefoot-engaged portions of said pad to shift and hold the toe of the patient in a displaced position from its normal position.

8. A toe protector device as specified in claim 6, wherein one of said hooked-type woven fabric end strip sections is fastened across the free outward end of the said projecting flap portion of said pad.

9. A toe protector device as specified in claim 8, wherein the other one of said hooked-type woven fabric end strip sections is fastened across the free outward end of that one of the said laterally extending wing portions of the pad projecting therefrom in a direction opposite to said flap portion.

10. A device according to claim 6 in which said hook/loop separable fastener means is made of Velcro ® material.

* * * * *